US012734154B2

(12) United States Patent
Ding et al.

(10) Patent No.: US 12,734,154 B2
(45) Date of Patent: Sep. 15, 2026

(54) EYE CARE COMPOSITION CONTAINING L-ERGOTHIONEINE, AND PREPARATION METHOD THEREFOR AND USE THEREOF

(71) Applicant: GENE III BIOTECHNOLOGY CO., LTD., Nanjing (CN)

(72) Inventors: Wei Ding, Nanjing (CN); Juan Cao, Nanjing (CN); Cong Guo, Nanjing (CN); Hongying Ju, Nanjing (CN); Rujun He, Nanjing (CN)

(73) Assignee: GENE III BIOTECHNOLOGY CO., LTD., Nanjing (CN)

( * ) Notice: Subject to any disclaimer, the term of this patent is extended or adjusted under 35 U.S.C. 154(b) by 0 days.

(21) Appl. No.: 19/081,581

(22) Filed: Mar. 17, 2025

(65) Prior Publication Data

US 2026/0027085 A1 Jan. 29, 2026

(30) Foreign Application Priority Data

Jul. 26, 2024 (CN) ......................... 202411015027.4

(51) Int. Cl.

| | |
|---|---|
| ***A61K 31/4172*** | (2006.01) |
| ***A61K 9/00*** | (2006.01) |
| ***A61K 31/205*** | (2006.01) |
| ***A61K 31/69*** | (2006.01) |
| ***A61K 31/728*** | (2006.01) |
| ***A61K 36/28*** | (2006.01) |
| ***A61K 36/534*** | (2006.01) |
| ***A61P 27/04*** | (2006.01) |

(52) U.S. Cl.

CPC ........ *A61K 31/4172* (2013.01); *A61K 9/0048* (2013.01); *A61K 31/205* (2013.01); *A61K 31/69* (2013.01); *A61K 31/728* (2013.01); *A61K 36/28* (2013.01); *A61K 36/534* (2013.01); *A61P 27/04* (2018.01)

(58) Field of Classification Search

None

See application file for complete search history.

(56) References Cited

U.S. PATENT DOCUMENTS

2014/0128615 A1* 5/2014 Yarosh ..................... A61K 8/19 548/324.1

FOREIGN PATENT DOCUMENTS

| | | | | |
|---|---|---|---|---|
| CN | 114410391 A | 4/2022 | | |
| CN | 114748611 A | 7/2022 | | |
| CN | 115068595 A | 9/2022 | | |
| WO | 2019/089878 A1 | 5/2019 | | |
| WO | WO-2020094244 A1 * | 5/2020 | ........... | C11D 3/2093 |

OTHER PUBLICATIONS

CN Office Action dated May 7, 2025 as received in Application No. 202411015027.8.

CN Decision to Grant Dated Jun. 2, 2025 as received in Application No. 202411015027.8.

* cited by examiner

*Primary Examiner* — Anand U Desai
*Assistant Examiner* — Catheryne Chen
(74) *Attorney, Agent, or Firm* — Maschoff Brennan

(57) ABSTRACT

Provided are an eye care composition containing L-ergothioneine and a preparation method therefor and use thereof. The eye care composition containing L-ergothioneine provided in the present application includes the following components: L-ergothioneine, taurine, sodium hyaluronate, plant essential oil, p-benzenediboronic acid, an osmotic pressure regulator and water for injection. The preparation method includes mixing the sodium hyaluronate and the water for injection to obtain solution A; mixing the solution A, the taurine, the L-ergothioneine and the p-benzenediboronic acid, and adjusting pH to 5-7.5 to obtain solution B; and mixing the solution B and the plant essential oil, adjusting osmotic pressure to 250-350 mOsm/(Kg·$H_2O$) by adding the osmotic pressure regulator, performing filtration and sterilization, and sub-packaging, so as to complete the preparation method. Based on the particular components and their proportions in the technical solutions of the present application, the eye care composition containing L-ergothioneine is obtained with the high stability, anti-inflammatory effect, relief effect on eye fatigue, itchy eyes and dry eyes, and good moisturizing effect.

10 Claims, No Drawings

EYE CARE COMPOSITION CONTAINING L-ERGOTHIONEINE, AND PREPARATION METHOD THEREFOR AND USE THEREOF

TECHNICAL FIELD

The present application belongs to the technical field of pharmaceuticals, and specifically relates to an eye care composition containing L-ergothioneine and a preparation method therefor and use thereof.

BACKGROUND

Frequent use of electronic products will easily cause eye fatigue, dry and sore eyes, weakening the eye's antioxidant defense system, and resulting in vision loss, blurred vision and in turn other eye diseases. Using eyewash to clean and care eyes, which contains natural active substances and is prepared as a compatible solution for human body with purified or distilled water and inorganic salts, has good performance in relieving eye fatigue, maintaining eye clean, alleviating some eye diseases, and repairing minimal physical damage in eyes, and meanwhile, the eyewash can stimulate the microvascular circulation of the eyes and satisfy the demand for nutrients of eye skin, alleviating the dark circle problem caused by fatigue, staying up late and poor sleep, etc., which is favored by consumers.

Chinese patent No. CN116889599A discloses a blueberry eyewash solution and a preparation method therefor in the field of eyewash technologies. Every 1000 mL of the eyewash solution is prepared from the following raw materials: 60-80 g of blueberries, 80-100 g of indigowoad leaves, 20-40 g of mulberry leaves, 2-3 g of vitamin complex, and 0.2-0.25 g of sodium hyaluronate, wherein the vitamin complex is any two of vitamin B6, vitamin B12, vitamin A, and vitamin E. The eyewash solution prepared by mixing blueberries, indigowoad leaves, mulberry leaves, vitamin complex and sodium hyaluronate has low-cost raw materials; the use of topical administration directly delivers the drug to the acting site, the absorption is fast, and the effect is obvious. However, the eyewash solution can relieve dryness only but does not have anti-fatigue or anti-inflammatory effects.

Chinese patent No. CN114099551B discloses a composition for eye fatigue relieving and eye moisturizing, the main components of which include glyceryl glucoside, zinc sulfate, tea polyphenols, taurine, dipotassium glycyrrhizinate, menthol, and borneolum syntheticum. The composition can be used in the eye-moistening spray and eyewash aqueous products, which not only has the relief effect on eye fatigue, eye itching, periocular dryness and dry eyes and eyesight-improving effect, but also has a good moisturizing effect, natural, safe and non-irritating components, and promising application prospect. However, the composition has complex components, and has not been tested for its stability.

Chinese patent No. CN114949035A discloses an eyewash solution for preventing dry eyes and a preparation method therefor. The eyewash solution is made of the following raw materials: 4-7 mg of taurine, 3-7 mg of borneolum syntheticum, 60-80 g of cornflower, 80-100 g of indigowoad leaves, 20-40 g of peppermint, 20-30 g of vitamin A, 6-8 mL of honey, and 6-8 mL of liquid pearl extract. The eyewash solution is a safe, effective and easy-to-use ophthalmic drug preparation for the clinical treatment of dry eyes. This product is only aiming at dry eye syndrome, which is undiversified, and cannot meet the needs of consumers with various eye symptoms.

On one hand, most of the common eyewash care products on the market only play a role in cleaning eyes, and their components are mostly chemicals, which are irritating to the eyes and have side effects in the long-term use. On the other hand, the eyewash or eye drops with anti-inflammatory, anti-allergic or vasoconstriction functions generally employ antibiotics, have strong side effects, bring discomfort problems to normal people, and are highly irritative to eyeballs. Moreover, the efficacy of the existing eyewash is usually quite single, which is only aiming at a certain eye symptom, but cannot meet the needs of consumers. Therefore, there is an urgent need to develop an eyewash solution that has natural and mild ingredients, multi-functional efficacies and good stability.

In view of the above, researchers of the present application have developed an eye care composition containing L-ergothioneine and a preparation method therefor. By optimizing the components and their proportions, an eyewash solution is obtained with the high stability, anti-inflammatory effect, relief effect on eye fatigue, itchy eyes and dry eyes, and good moisturizing effect.

SUMMARY

The present application provides an eye care composition containing L-ergothioneine and a preparation method therefor. The eye care composition includes L-ergothioneine, taurine, sodium hyaluronate, plant essential oil, a bacteriostat and an osmotic pressure regulator. Based on the synergistic effects and specific ratios of the components, the eye care composition containing L-ergothioneine is obtained with the high stability, anti-inflammatory effect, relief effect on eye fatigue, itchy eyes and dry eyes, and good moisturizing effect.

In a first aspect, the present application provides an eye care composition containing L-ergothioneine including the following components: L-ergothioneine, taurine, sodium hyaluronate, plant essential oil, p-benzenediboronic acid, an osmotic pressure regulator and water for injection.

Preferably, the L-ergothioneine, the taurine and the p-benzenediboronic acid have a mass ratio of 70-120:190-210:1; further preferably, the L-ergothioneine, the taurine and the p-benzenediboronic acid have a mass ratio of 90-100:190-250:1.

Preferably, the taurine, the sodium hyaluronate and the plant essential oil have a mass ratio of 10-25:1-10:1; further preferably, the taurine, the sodium hyaluronate and the plant essential oil have a mass ratio of 16-20:4-7:1.

Preferably, the eye care composition containing L-ergothioneine includes, in parts by weight, the following components: 0.01-1 parts of the L-ergothioneine, 0.1-5 parts of the taurine, 0.05-0.4 parts of the sodium hyaluronate, 0.03-0.06 parts of the plant essential oil, 0.001-0.004 parts of the p-benzenediboronic acid and 0.1-0.5 parts of the osmotic pressure regulator, and the water for injection added to complement 100 parts by weight.

Preferably, the eye care composition containing L-ergothioneine includes, in parts by weight, the following components: 0.25-0.42 parts of the L-ergothioneine, 0.6-1.2 parts of the taurine, 0.2-0.4 parts of the sodium hyaluronate, 0.03-0.06 parts of the plant essential oil, 0.001-0.004 parts of the p-benzenediboronic acid and 0.1-0.5 parts of the osmotic pressure regulator, and the water for injection added to complement 100 parts by weight.

Further preferably, the eye care composition containing L-ergothioneine includes, in parts by weight, the following components: 0.3-0.4 parts of the L-ergothioneine, 0.65-1.0 parts of the taurine, 0.22-0.38 parts of the sodium hyaluronate, 0.035-0.055 parts of the plant essential oil, 0.002-0.004 parts of the p-benzenediboronic acid and 0.2-0.5 parts of the osmotic pressure regulator, and the water for injection added to complement 100 parts by weight.

More preferably, the eye care composition containing L-ergothioneine includes, in parts by weight, the following components: 0.3-0.35 parts of the L-ergothioneine, 0.7-0.8 parts of the taurine, 0.22-0.3 parts of the sodium hyaluronate, 0.04-0.05 parts of the plant essential oil, 0.003-0.004 parts of the p-benzenediboronic acid and 0.3-0.5 parts of the osmotic pressure regulator, and the water for injection added to complement 100 parts by weight.

Preferably, the eye care composition containing L-ergothioneine further includes a pH adjusting agent.

Preferably, the eye care composition containing L-ergothioneine has a pH of 5-7.5.

Preferably, the pH adjusting agent is selected from at least one of a citrate buffer and a borate buffer; further preferably, the pH adjusting agent is the citrate buffer.

Preferably, the plant essential oil is selected from at least one of rose essential oil, chamomile essential oil and peppermint essential oil; further preferably, the plant essential oil is selected from at least one of the chamomile essential oil and the peppermint essential oil; more preferably, the plant essential oil is the chamomile essential oil and the peppermint essential oil.

Preferably, the chamomile essential oil and the peppermint essential oil have a mass ratio of 1-6:2-4; further preferably, the chamomile essential oil and the peppermint essential oil have a mass ratio of 4-6:2-3; more preferably, the chamomile essential oil and the peppermint essential oil have a mass ratio of 5:2.

Preferably, the osmotic pressure regulator is selected from at least one of sodium chloride, potassium chloride, sorbitol, borax and boric acid; further preferably, the osmotic pressure regulator is selected from at least one of sodium chloride and potassium chloride; more preferably, the osmotic pressure regulator is selected from sodium chloride.

In a second aspect, the present application provides a preparation method for the eye care composition containing L-ergothioneine described in the first aspect, including the following steps:

S1: mixing the sodium hyaluronate and the water for injection to obtain solution A;

S2: mixing the solution A, the taurine, the L-ergothioneine and the p-benzenediboronic acid, and adjusting pH to 5-7.5 to obtain solution B; and S3: mixing the solution B and the plant essential oil, adjusting osmotic pressure to 250-350 mOsm/($Kg \cdot H_2O$) by adding the osmotic pressure regulator, performing filtration and sterilization, and sub-packaging, so as to complete the preparation method.

Preferably, the mixing of S1 is performed at a temperature of 75-85° C.; further preferably, the mixing is performed at a temperature of 80° C.

Preferably, the mixing of S1 is stirring.

Preferably, the mixing of S2 is performed at a temperature of 35-45° C.; further preferably, the mixing of S2 is performed at a temperature of 35° C.

Preferably, the mixing of S2 may be selected from at least one of stirring and sonication; further preferably, the mixing of S2 is sonication.

Preferably, the mixing of S3 is performed at a temperature of 30-35° C.; further preferably, the mixing of S3 is performed at a temperature of 30° C.

Preferably, the mixing of S3 may be selected from at least one of stirring and sonication; further preferably, the mixing of S3 is stirring.

In a third aspect, the present application provides use of the eye care composition containing L-ergothioneine described in the first aspect in eye care.

Compared with the prior art, the present application has the following beneficial effects.

1. It is found in the present application by research that the L-ergothioneine, taurine and p-benzenediboronic acid have a synergistic effect in improving the antioxidant effect, and especially, with the specific ratios in the technical solutions of the present application, the three components significantly improves the antioxidant performance of the eye care composition containing L-ergothioneine;
2. It is found in the present application by research that the taurine, sodium hyaluronate and plant essential oil have a synergistic effect in eye relief and anti-fatigue effects, and especially, with the specific ratios in the technical solutions of the present application, the three components significantly improves the anti-fatigue effect of the eye care composition containing L-ergothioneine;
3. It is found in the present application by research that the taurine and p-benzenediboronic acid have a synergistic effect in improving the bacteriostatic effect, and especially, with the specific ratios in the technical solutions of the present application, the two components significantly improves the bacteriostatic effect of the eye care composition containing L-ergothioneine.
4. Based on the particular components and their proportions in the technical solutions of the present application, the eye care composition containing L-ergothioneine is obtained with the high stability, anti-inflammatory effect, relief effect on eye fatigue, itchy eyes and dry eyes, and good moisturizing effect.

DETAILED DESCRIPTION

In order to facilitate the understanding of the technical means, creative features, purposes and effects in the present application, the present application is further elucidated hereinafter in terms of specific examples. However, the examples below are only the preferred examples of the present application, not all the examples. Other examples obtained by those skilled in the art without creative efforts based on the examples in the embodiments shall fall within the protection scope of the present application. It is worth noting that all raw materials used in the present application are commercially available products, and their sources are not specifically limited. The technical and scientific terms used in the examples have the meanings commonly understood by those skilled in the art to which the present application pertains.

Example 1

1) Components

In parts by weight, the following components are contained: 0.35 parts of L-ergothioneine, 0.75 parts of taurine, 0.25 parts of sodium hyaluronate, 0.03 parts of chamomile essential oil, 0.012 parts of peppermint essential oil, 0.0036 parts of p-benzenediboronic acid, and 0.44 parts of sodium chloride, and water for injection added to complement 100 parts by weight.

2) Preparation

S1: Sodium hyaluronate was dissolved with water for injection at 80° C. by stirring to obtain solution A;

S2: the solution A, taurine, L-ergothioneine and p-benzenediboronic acid were sonicated at 35° C. for 20 min, and an appropriate amount of citrate buffer was added to adjust the pH to 5-7.5 to obtain solution B; and S3: the solution B and plant essential oil were stirred at 30° C., mixed uniformly, added with sodium chloride to adjust the osmotic pressure to 310 mOsm/(Kg·$H_2O$), subjected to filtration and sterilization, and sub-packaged, so as to complete the preparation.

Example 2

Compared with Example 1, only the components are changed, specifically including:

1) Components

In parts by weight, the following components are contained: 0.12 parts of L-ergothioneine, 0.19 parts of taurine, 0.05 parts of sodium hyaluronate, 0.021 parts of chamomile essential oil, 0.009 parts of peppermint essential oil, 0.001 parts of p-benzenediboronic acid, and 0.5 parts of sodium chloride, and water for injection added to complement 100 parts by weight.

The other operations are the same as in Example 1.

Example 3

Compared with Example 1, only the components are changed, specifically including:

1) Components

In parts by weight, the following components are contained: 0.4 parts of L-ergothioneine, 1.0 parts of taurine, 0.4 parts of sodium hyaluronate, 0.043 parts of chamomile essential oil, 0.017 parts of peppermint essential oil, 0.004 parts of p-benzenediboronic acid, and 0.1 parts of sodium chloride, and water for injection added to complement 100 parts by weight.

The other operations are the same as in Example 1.

Comparative Example 1

Compared with Example 1, only the components are changed, and L-ergothioneine is replaced with taurine, specifically including:

In parts by weight, the following components are contained: 1.1 parts of taurine, 0.25 parts of sodium hyaluronate, 0.03 parts of chamomile essential oil, 0.012 parts of peppermint essential oil, 0.0036 parts of p-benzenediboronic acid, and 0.44 parts of sodium chloride, and water for injection added to complement 100 parts by weight.

The other operations are the same as in Example 1.

Comparative Example 2

Compared with Example 1, only the components are changed, and L-ergothioneine is replaced with p-benzenediboronic acid, specifically including:

In parts by weight, the following components are contained: 0.3536 parts of p-benzenediboronic acid, 0.75 parts of taurine, 0.25 parts of sodium hyaluronate, 0.03 parts of chamomile essential oil, 0.012 parts of peppermint essential oil, and 0.44 parts of sodium chloride, and water for injection added to complement 100 parts by weight.

The other operations are the same as in Example 1.

Comparative Example 3

Compared with Example 1, only the components are changed, and p-benzenediboronic acid is replaced with taurine, specifically including:

In parts by weight, the following components are contained: 0.35 parts of L-ergothioneine, 0.7536 parts of taurine, 0.25 parts of sodium hyaluronate, 0.03 parts of chamomile essential oil, 0.012 parts of peppermint essential oil, and 0.44 parts of sodium chloride, and water for injection added to complement 100 parts by weight.

The other operations are the same as in Example 1.

Comparative Example 4

Compared with Example 1, only the components are changed, and p-benzenediboronic acid is replaced with dipotassium glycyrrhizinate, specifically including:

In parts by weight, the following components are contained: 0.35 parts of L-ergothioneine, 0.75 parts of taurine, 0.25 parts of sodium hyaluronate, 0.03 parts of chamomile essential oil, 0.012 parts of peppermint essential oil, 0.0036 parts of dipotassium glycyrrhizinate, and 0.44 parts of sodium chloride, and water for injection added to complement 100 parts by weight.

The other operations are the same as in Example 1.

Comparative Example 5

Compared with Example 1, only the components are changed, and p-benzenediboronic acid is replaced with p-hydroxybenzoate, specifically including:

In parts by weight, the following components are contained: 0.35 parts of L-ergothioneine, 0.75 parts of taurine, 0.25 parts of sodium hyaluronate, 0.03 parts of chamomile essential oil, 0.012 parts of peppermint essential oil, 0.0036 parts of p-hydroxybenzoate, and 0.44 parts of sodium chloride, and water for injection added to complement 100 parts by weight.

The other operations are the same as in Example 1.

Comparative Example 6

Compared with Example 1, only the components are changed, and p-benzenediboronic acid is replaced with benzalkonium chloride, specifically including:

In parts by weight, the following components are contained: 0.35 parts of L-ergothioneine, 0.75 parts of taurine, 0.25 parts of sodium hyaluronate, 0.03 parts of chamomile essential oil, 0.012 parts of peppermint essential oil, 0.0036 parts of benzalkonium chloride, and 0.44 parts of sodium chloride, and water for injection added to complement 100 parts by weight.

The other operations are the same as in Example 1.

Comparative Example 7

Compared with Example 1, only the components are changed, and p-benzenediboronic acid is replaced with thimerosal, specifically including:

In parts by weight, the following components are contained: 0.35 parts of L-ergothioneine, 0.75 parts of taurine, 0.25 parts of sodium hyaluronate, 0.03 parts of chamomile essential oil, 0.012 parts of peppermint essential oil, 0.0036 parts of thimerosal, and 0.44 parts of sodium chloride, and water for injection added to complement 100 parts by weight.

The other operations are the same as in Example 1.

Comparative Example 8

Compared with Example 1, only the components are changed, and taurine is replaced with sodium hyaluronate, specifically including:

In parts by weight, the following components are contained: 0.35 parts of L-ergothioneine, 1 part of sodium hyaluronate, 0.03 parts of chamomile essential oil, 0.012 parts of peppermint essential oil, 0.0036 parts of p-benzenediboronic acid, and 0.44 parts of sodium chloride, and water for injection added to complement 100 parts by weight.

The other operations are the same as in Example 1.

Comparative Example 9

Compared with Example 1, only the components are changed, and plant essential oil is replaced with sodium hyaluronate, specifically including:

In parts by weight, the following components are contained: 0.35 parts of L-ergothioneine, 0.75 parts of taurine, 0.292 parts of sodium hyaluronate, 0.0036 parts of p-benzenediboronic acid, and 0.44 parts of sodium chloride, and water for injection added to complement 100 parts by weight.

The other operations are the same as in Example 1.

Comparative Example 10

Compared with Example 1, only the components are changed, and peppermint essential oil is replaced with chamomile essential oil, specifically including:

In parts by weight, the following components are contained: 0.35 parts of L-ergothioneine, 0.75 parts of taurine, 0.25 parts of sodium hyaluronate, 0.042 parts of chamomile essential oil, 0.0036 parts of p-benzenediboronic acid, and 0.44 parts of sodium chloride, and water for injection added to complement 100 parts by weight.

The other operations are the same as in Example 1.

Comparative Example 11

Compared with Example 1, only the components are changed, and plant essential oil is removed, specifically including:

In parts by weight, the following components are contained: 0.35 parts of L-ergothioneine, 0.75 parts of taurine, 0.25 parts of sodium hyaluronate, 0.0036 parts of p-benzenediboronic acid, and 0.44 parts of sodium chloride, and water for injection added to complement 100 parts by weight.

The other operations are the same as in Example 1.

Comparative Example 12

Compared with Example 1, only the proportions of components are changed, specifically including:

In parts by weight, the following components are contained: 0.1 parts of L-ergothioneine, 1.5 parts of taurine, 0.05 parts of sodium hyaluronate, 0.11 parts of chamomile essential oil, 0.01 parts of peppermint essential oil, 0.0056 parts of p-benzenediboronic acid, and 0.060 parts of sodium chloride, and water for injection added to complement 100 parts by weight.

The other operations are the same as in Example 1.

Comparative Example 13

Compared with Example 1, only the preparation method is changed, specifically including:

The components are the same as in Example 1;

Preparation:

The L-ergothioneine, taurine, sodium hyaluronate, p-benzenediboronic acid, chamomile essential oil, peppermint essential oil and water for injection were stirred and mixed, added with an appropriate amount of citrate buffer to adjust the pH to 5-7.5, added with sodium chloride to adjust the osmotic pressure to 310 mOsm/(Kg·$H_2O$), subjected to filtration and sterilization, and sub-packaged, so as to complete the preparation.

Test Example 1

In Vitro Antioxidant Assay

Daily contact lens wear leads to inadequate oxygen supply and causes excessive generation of ROS free radicals, especially, accumulation of superoxide anion ($O^{2-}$). The eye care compositions containing L-ergothioneine prepared in Examples 1-3 and Comparative Examples 1-13 are tested for the antioxidant performance. The superoxide anion is determined by the pyrogallol autoxidation method, and the hydroxyl radical scavenging assay is performed by the Fenton colorimetric method, and the DPPH radical scavenging assay is the most widely used method for indirectly detecting the antioxidant capacity of the substance under test. The above reactions are used to determine the antioxidant performance of the substance under test by detecting the change in absorbance. The results are shown in Tables 1-3.

TABLE 1

Results of $O^{2-}$ inhibition rate

| Examples | $O^{2-}$ inhibition rate/% | Hydroxyl radical scavenging rate/% | DPPH inhibition rate/% |
|---|---|---|---|
| Example 1 | 99.5 | 65.4 | 99.4 |
| Example 2 | 99.2 | 63.7 | 99.0 |
| Example 3 | 99.3 | 62.5 | 99.1 |
| Comparative Example 1 | 34.5 | 24.3 | 43.6 |
| Comparative Example 2 | 33.6 | 20.9 | 40.9 |
| Comparative Example 3 | 52.1 | 30.2 | 64.3 |
| Comparative Example 4 | 38.2 | 22.1 | 42.2 |
| Comparative Example 5 | 37.4 | 20.7 | 44.7 |
| Comparative Example 6 | 31.9 | 25.7 | 41.6 |
| Comparative Example 7 | 35.2 | 21.4 | 40.2 |
| Comparative Example 8 | 47.1 | 29.8 | 63.7 |
| Comparative Example 9 | 54.8 | 32.5 | 63.1 |
| Comparative Example 10 | 61.5 | 34.7 | 67.2 |
| Comparative Example 11 | 52.4 | 33.6 | 61.8 |
| Comparative Example 12 | 31.6 | 20.3 | 43.4 |
| Comparative Example 13 | 82.9 | 58.5 | 79.5 |

As shown in Table 1, the eye care composition containing L-ergothioneine prepared by the technical solutions of the present application has a better antioxidant effect, which is significantly superior than the comparative examples; the L-ergothioneine, taurine and p-benzenediboronic acid have a synergistic effect in improving the antioxidant effect especially in the particular ratios of the technical solutions of the present application, which significantly improves the antioxidant performance of the eye care composition containing L-ergothioneine.

Test Example 2

Cytotoxicity Assay

A corneal stromal cell suspension at a concentration of $1\times10^5$ cells/mL was added to a 96-well plate by 100 μL/well and cultured for 24 h in an incubator containing 5% $CO_2$ at 37° C., and the culture medium was then pipetted out. The eye care compositions containing L-ergothioneine prepared in Examples 1-3 and Comparative Examples 1-13 and the complete medium were added to the 96-well plate at a ratio of 1:10, and the cells were cultured for another 24 h. The positive control (10% DMSO), negative control (complete cell culture medium) and eye care composition containing L-ergothioneine prepared in Examples 1-3 and Comparative Examples 1-13 all had 6 replicates. The cells continued to be cultured for 3 h after added with MTT (20 μL/well). Subsequently, 100 μL DMSO was added and shaken for 10 min, and the absorbance value was determined at 570 nm by a microplate reader. Cell activity was calculated:

$$\text{Cell activity} = (OD \text{ value of test substance well} - OD \text{ value of blank control well}) / OD \text{ value of negative control well}.$$

The results are shown in Table 2.

TABLE 2

Results of cytotoxicity assay

| Examples | 24 h Survival rate of corneal stromal cell/% | 72 h Survival rate of corneal stromal cell/% |
|---|---|---|
| Example 1 | 100 | 98.5 |
| Example 2 | 99.9 | 98.0 |
| Example 3 | 99.9 | 98.2 |
| Comparative Example 1 | 99.8 | 98.1 |
| Comparative Example 2 | 99.2 | 98.4 |
| Comparative Example 3 | 99.3 | 98.3 |
| Comparative Example 4 | 99.7 | 98.0 |
| Comparative Example 5 | 99.5 | 98.4 |
| Comparative Example 6 | 99.5 | 98.3 |
| Comparative Example 7 | 99.8 | 97.9 |
| Comparative Example 8 | 99.0 | 98.5 |
| Comparative Example 9 | 99.7 | 98.1 |
| Comparative Example 10 | 99.2 | 98.2 |
| Comparative Example 11 | 99.5 | 98.4 |
| Comparative Example 12 | 99.7 | 98.3 |
| Comparative Example 13 | 99.1 | 98.0 |

As can be seen from the data in Table 2, the 24 h survival rate of corneal stromal cell of all the products is 99% or more, and the 72 h survival rate of corneal stromal cell is 98% or more, indicating that the eye care compositions containing L-ergothioneine prepared according to examples and comparative examples are safe and non-toxic to the corneal stromal cell.

Test Example 3

Bacterial Inhibition Effect

By using *Escherichia coli, Staphylococcus aureus, Pseudomonas aeruginosa*, and *Candida albicans* as four test strains, the eye care compositions containing L-ergothioneine prepared in Examples 1-3 and Comparative Examples 1-13 are tested for the bacteriostatic effect.

Preparation of bacterial suspension for experiment: *Pseudomonas aeruginosa, Staphylococcus aureus, Escherichia coli* and *Candida albicans* were cultured with agar medium. An appropriate amount of 0.9% sterile sodium chloride solution was added to remove the culture substance from the surface of agar, and the bacterial suspension was transferred to a sterile test tube, diluted with 0.9% sterile sodium chloride solution and prepared as a bacterial suspension containing about 108 cfu of bacteria per 1 mL. The bacterial suspension for experiment was taken by 0.5 mL, added to a test tube, then added with 0.5 mL of organic interfering substance (3% bovine serum protein solution), mixed uniformly, and placed in a water bath at 20° C.±1° C. for 5 min; then the eye care compositions containing L-ergothioneine prepared in Examples 1-3 and Comparative Examples 1-13 were taken by 4.0 mL separately with a sterile pipette and injected to the test tube, mixed rapidly and timed immediately.

After the test bacteria interacted with the samples of each Example and Comparative Example for a predetermined period, 0.5 mL of the mixture of test bacteria and sample was pipetted out independently, added to 4.5 mL of sterilized neutralizing agent, and mixed uniformly. After 10 min action of the neutralizing agent in the mixture of test bacteria and sample in each tube, 1.0 mL of sample solution was pipetted out, and determined for the number of viable bacteria by the viable bacteria culture counting method; each sample solution was inoculated on two Petri dishes. If there were too many colonies growing on the plate, a series of 10-fold dilution could be carried out, and then the viable bacteria culture count was performed. At the same time, the diluted solution was used instead of the sample to perform the parallel test as a control.

All the test samples were cultured in a 37° C. incubator. The bacterial vegetative cells were cultured for 48 h to observe the final result; the bacterial spores were cultured for 72 h to observe the final result. The test was repeated 3 times, and the number of viable bacteria in each group was counted, and then the inhibition rate was calculated according to the following formula:

$$\text{Inhibition rate} = (\text{number of viable bacteria in control group} - \text{number of viable bacteria in test group}) / \text{number of viable bacteria in control group} \times 100\%.$$

The results are shown in Table 3.

TABLE 3

Bacterial inhibition effect

| Groups | Inhibition rate/% Strains *Escherichia coli* | *Staphylococcus aureus* | *Pseudomonas aeruginosa* | *Candida albicans* |
|---|---|---|---|---|
| Example 1 | 99.8 | 99.9 | 99.7 | 99.6 |
| Example 2 | 99.5 | 99.7 | 99.2 | 99.7 |
| Example 3 | 99.2 | 99.5 | 99.6 | 99.3 |
| Comparative Example 1 | 54.2 | 56.8 | 51.0 | 55.7 |
| Comparative Example 2 | 50.2 | 49.7 | 51.6 | 52.3 |
| Comparative Example 3 | 51.4 | 52.8 | 51.6 | 50.2 |
| Comparative | 50.8 | 48.2 | 51.2 | 51.4 |

TABLE 3-continued

Bacterial inhibition effect

| Groups | Inhibition rate/% Strains *Escherichia coli* | *Staphylococcus aureus* | *Pseudomonas aeruginosa* | *Candida albicans* |
|---|---|---|---|---|
| Example 4 | | | | |
| Comparative Example 5 | 49.2 | 50.1 | 48.5 | 49.7 |
| Comparative Example 6 | 48.9 | 49.5 | 50.2 | 49.7 |
| Comparative Example 7 | 49.2 | 50.5 | 48.4 | 50.1 |
| Comparative Example 8 | 53.8 | 51.7 | 52.9 | 54.2 |
| Comparative Example 9 | 68.2 | 67.4 | 69.5 | 68.3 |
| Comparative Example 10 | 70.5 | 69.8 | 66.4 | 65.9 |
| Comparative Example 11 | 65.8 | 65.1 | 62.4 | 63.7 |
| Comparative Example 12 | 48.2 | 50.6 | 49.3 | 51.7 |
| Comparative Example 13 | 67.5 | 68.2 | 70.8 | 69.3 |

As shown in Table 3, the eye care composition containing L-ergothioneine prepared by the technical solutions of the present application has a better bacterial inhibition effect, which is significantly superior than the comparative examples; the taurine and p-benzenediboronic acid have a synergistic effect in improving the antioxidant effect especially in the particular ratios of the technical solutions of the present application, which significantly improves the bacterial inhibition effect of the eye care composition containing L-ergothioneine.

Test Example 4

In Vivo Experiment:

1. Retention Time Experiment

The eye care compositions containing L-ergothioneine prepared in Examples 1-3 and Comparative Examples 1-13 were added with 2% sodium fluorescein and mixed thoroughly. New Zealand rabbits were used as experimental subjects, and randomly divided into 16 groups (6 rabbits for each group); and there was no significant difference in the age and weight of the rabbits in each group. The above different eye care composition containing L-ergothioneine was added dropwise by 30 μL to the rabbit eye by opening the eyelid on one side, and then the rabbit eye was closed manually for 10 s. Subsequently, the eye was illuminated with a UV lamp every 2 min. The intensity of continuous fluorescent layer on the surface of cornea was observed, and the time which the continuous fluorescent layer took to disappear was defined as the eye retention time. The average of the three consecutive determinations was taken as the eye retention time, and the results are shown in Table 4.

TABLE 4

Eye retention time

| Determination | Time/min First | Second | Third | Average time/min |
|---|---|---|---|---|
| Example 1 | 28.2 | 27.9 | 28.5 | 28.2 |
| Example 2 | 27.8 | 28.5 | 28.0 | 28.1 |
| Example 3 | 28.4 | 28.1 | 27.1 | 27.9 |
| Comparative Example 1 | 12.2 | 11.9 | 11.5 | 11.9 |
| Comparative Example 2 | 10.8 | 11.2 | 10.5 | 10.8 |
| Comparative Example 3 | 12.5 | 11.6 | 11.7 | 11.9 |
| Comparative Example 4 | 11.5 | 12.8 | 12.4 | 12.2 |
| Comparative Example 5 | 10.3 | 11.4 | 10.9 | 10.9 |
| Comparative Example 6 | 12.2 | 11.8 | 11.7 | 11.9 |
| Comparative Example 7 | 13.5 | 12.8 | 13.1 | 13.1 |
| Comparative Example 8 | 21.2 | 20.9 | 21.5 | 21.2 |
| Comparative Example 9 | 20.7 | 21.4 | 21.6 | 21.2 |
| Comparative Example 10 | 13.7 | 12.4 | 12.8 | 13.0 |
| Comparative Example 11 | 10.8 | 10.5 | 10.7 | 10.7 |
| Comparative Example 12 | 11.2 | 10.4 | 10.1 | 10.6 |
| Comparative Example 13 | 20.4 | 19.8 | 20.5 | 20.2 |

As can be seen from the data in Table 4, the retention time of the eye care composition containing L-ergothioneine prepared by the technical solutions of the present application is significantly increased when compared with the eye care composition containing L-ergothioneine prepared in the comparative examples, indicating that the specific components and ratios and the preparation method of the technical solutions of the present application improve the bio-availability of the eye care composition containing L-ergothioneine.

2. Animal Experiment of Dry Eye

1 Experimental Material 1.1 Animals:

Ninety-five SPF BALB/c male mice, 6-8 weeks old, body mass (21±3) g. The animals were fed for 1 week for acclimatization after accommodated in the animal house, during which period food and water were available ad libitum, the temperature was (24±2° C.) and humidity was 47%.

1.2 Modeling Method for Dry Eye Animal Model

Five mice were taken as the blank group and injected with saline every day; the remaining 90 mice were modeled, and a 0.2% benzalkonium chloride solution were added dropwise to their eyes to establish a mouse model of benzalkonium chloride-induced dry eye (5 μL/each eye, one time each day). After 6 weeks of eye administration, tear secretion and tear break-up time (BUT) were tested to evaluate the modeling status of the mice, and the unqualified mice were excluded.

Modeling results of 90 mice: 85 mice were successfully modeled and 5 mice were failed. The successfully-modeled 85 mice were randomly grouped (5 mice for each group) into 17 groups in total (16 test groups, including Examples 1-3 and Comparative Examples 1-13), one of which was the model group.

1.3 Administration:

For the blank group, each mouse was dropped with 0.2 mL of sterilized saline on the left and right eyes independently, twice one day;

For test groups 1-16 (corresponding to Examples 1-3 and Comparative Examples 1-13, respectively), each mouse was dropped with 0.2 mL of the eye care composition containing L-ergothioneine prepared in Examples 1-3 and Comparative Examples 1-13 on the left and right eyes independently, twice one day;

Each mouse in the model group was dropped with 0.2 mL of sterilized saline on the left and right eyes independently, twice one day;

The administration was carried out for 28 days consecutively, and the indicator was observed.

1.4 Indicator Observation:

1) Tear Secretion

After modeling, mice were tested for tear secretion using tear secretion test paper (SchirmerItest, SIT) to evaluate whether the model was formed. After drug intervention, mice were tested again for tear secretion using tear secretion test paper to evaluate the effect of the intervening drug on tear secretion in mice.

2) Test of Tear Break-Up Time

After modeling, the fluorescein staining method was used to observe the BUT of mice to evaluate whether the model was formed. After drug intervention, BUT was tested again to evaluate the effect of the intervening drug on tear secretion in mice.

3) Immunofluorescence was used to detect the expression levels of interleukin (IL)-1β, IL-6 and tumor necrosis factor-α (TNF-α) in corneal tissues of mice in each group. After 4 weeks of drug administration, the mice were over-anesthetized and euthanized. The eyeballs were harvested and quickly fixed in 4% paraformaldehyde for immunofluorescence detection at a later stage. The fixed eyeballs were taken out, subjected to dehydration by an automatic paraffin dehydrator, then embedded, sectioned, dewaxed, and baked, then the thermal recovery method was performed for antigen recovery, 5% BSA was used for blocking followed by PBS washing, and the primary antibody and Alexa Fluor 488-labeled secondary antibody were added dropwise. Finally, the optical microscope was used for observation and the average optical density values in 4 random fields were calculated for statistics.

1.5 Statistical Analysis:

SPSS16.0 statistical software was used for analysis and processing, data were expressed as (x±s), and one-way ANOVA was used for group comparison. The results are shown in Table 5.

TABLE 5

Results of animal experiment of dry eye

| Groups | Tear secretion/mm | Tear break-up time/s | IL-1β | IL-6 | TNF-α |
|---|---|---|---|---|---|
| Blank group | 5.8 ± 0.04 | 6.2 ± 0.02 | 6.1 ± 0.53 | 5.8 ± 0.74 | 4.0 ± 0.28 |
| Test Example 1 | 5.5 ± 0.09 | 5.8 ± 0.05 | 45.2 ± 0.24** | 39.4 ± 0.11** | 30.4 ± 0.85** |
| Test Example 2 | 5.4 ± 0.01 | 5.7 ± 0.04 | 47.6 ± 0.58** | 41.3 ± 0.44** | 35.2 ± 0.25** |
| Test Example 3 | 5.4 ± 0.02 | 5.5 ± 0.01 | 46.2 ± 0.10** | 40.2 ± 0.77** | 33.1 ± 0.22** |
| Test Example 4 | 3.2 ± 0.08 | 3.3 ± 0.10 | 105.7 ± 1.8* | 91.5 ± 2.4* | 82.2 ± 1.2* |
| Test Example 5 | 3.3 ± 0.04 | 3.1 ± 0.06 | 110.2 ± 2.4* | 90.8 ± 4.3* | 85.3 ± 1.7* |
| Test Example 6 | 3.1 ± 0.03 | 3.2 ± 0.01 | 107.2 ± 3.4* | 95.1 ± 0.5* | 80.2 ± 3.6* |
| Test Example 7 | 3.3 ± 0.05 | 3.0 ± 0.07 | 109.1 ± 1.2* | 96.4 ± 2.5* | 86.7 ± 2.2* |
| Test Example 8 | 3.2 ± 0.04 | 3.1 ± 0.02 | 115.5 ± 4.1* | 90.2 ± 0.4* | 84.2 ± 1.7* |
| Test Example 9 | 3.1 ± 0.01 | 3.2 ± 0.06 | 105.4 ± 2.6* | 92.2 ± 4.1* | 80.9 ± 0.8* |
| Test Example 10 | 3.0 ± 0.02 | 3.3 ± 0.04 | 117.6 ± 2.3* | 90.3 ± 4.6* | 82.5 ± 2.3* |
| Test Example 11 | 3.4 ± 0.07 | 3.1 ± 0.05 | 108.5 ± 1.0* | 91.8 ± 0.2* | 81.6 ± 1.8.* |
| Test Example 12 | 3.3 ± 0.08 | 3.2 ± 0.07 | 104.3 ± 5.2* | 92.5 ± 1.3* | 82.5 ± 3.2* |
| Test Example 13 | 3.1 ± 0.02 | 3.0 ± 0.04 | 117.2 ± 0.9* | 94.8 ± 3.6* | 82.5 ± 2.7* |
| Test Example 14 | 3.0 ± 0.07 | 3.4 ± 0.01 | 102.5 ± 5.8* | 95.4 ± 2.2* | 80.5 ± 1.2* |
| Test Example 15 | 3.4 ± 0.03 | 3.2 ± 0.06 | 107.6 ± 3.3* | 94.2 ± 0.7* | 80.4 ± 0.2* |
| Test Example 16 | 3.1 ± 0.04 | 3.3 ± 0.01 | 121.7 ± 5.6* | 96.8 ± 2.7* | 85.3 ± 3.9* |
| Model group | 2 ± 0.12 | 2.7 ± 0.09 | 185.3 ± 1.8 | 170.5 ± 3.6 | 162.7 ± 2.2 |

Note:

Test Examples 1-3 correspond to Examples 1-3; Test Examples 4-16 correspond to Comparative Examples 4-16; Comparison with the model group: **P < 0.01; *P < 0.05.

As can be seen from the data in Table 5, the anti-inflammatory and moisturizing performance of the eye care composition containing L-ergothioneine prepared by the technical solutions of the present application are significantly improved compared with those prepared in the comparative examples, indicating that the specific components and ratios and the preparation method of the technical solutions of the present application improve the eye care composition containing L-ergothioneine in its anti-inflammatory performance, relief effect, etc.

Finally, it should be noted that the above content is only used to illustrate the technical solutions of the present application, but not limit the protection scope of the present application. Simple modifications or equivalent substitutions of the technical solutions of the present application made by those skilled in the art will not depart from the substance and scope of the technical solutions of the present application.

What is claimed is:

1. An eye care composition containing L-ergothioneine, comprising the following components: in parts by weight, the following components: 0.01-1 parts of the L-ergothioneine, 0.1-5 parts of the taurine, 0.05-0.4 parts of the sodium hyaluronate, 0.03-0.06 parts of the plant essential oil, 0.001-0.004 parts of the p-benzenediboronic acid and 0.1-0.5 parts of the osmotic pressure regulator, and the water for injection added to complement 100 parts by weight; wherein the L-ergothioneine, the taurine and the p-benzenediboronic acid have a weight ratio of 70-120:190-250:1.

2. The eye care composition containing L-ergothioneine according to claim 1, wherein the taurine, the sodium hyaluronate and the plant essential oil have a weight ratio of 10-25:1-10:1.

3. The eye care composition containing L-ergothioneine according to claim 1, wherein the eye care composition containing L-ergothioneine comprises, in parts by weight, the following components: 0.25-0.42 parts of the L-ergothioneine, 0.6-1.2 parts of the taurine, 0.2-0.4 parts of the sodium hyaluronate, 0.03-0.06 parts of the plant essential oil, 0.001-0.004 parts of the p-benzenediboronic acid and 0.1-0.5 parts of the osmotic pressure regulator, and the water for injection added to complement 100 parts by weight.

4. The eye care composition containing L-ergothioneine according to claim 3, wherein the eye care composition containing L-ergothioneine comprises, in parts by weight, the following components: 0.3-0.35 parts of the L-ergothioneine, 0.7-0.8 parts of the taurine, 0.22-0.3 parts of the sodium hyaluronate, 0.04-0.05 parts of the plant essential oil, 0.003-0.004 parts of the p-benzenediboronic acid and 0.3-0.5 parts of the osmotic pressure regulator, and the water for injection added to complement 100 parts by weight.

5. The eye care composition containing L-ergothioneine according to claim 1, wherein the eye care composition containing L-ergothioneine further comprises a pH adjusting agent.

6. The eye care composition containing L-ergothioneine according to claim 1, wherein the eye care composition containing L-ergothioneine has a pH of 5-7.5.

7. The eye care composition containing L-ergothioneine according to claim 5, wherein the pH adjusting agent is selected from at least one of a citrate buffer and a borate buffer.

8. The eye care composition containing L-ergothioneine according to claim 1, wherein the plant essential oil is selected from at least one of rose essential oil, chamomile essential oil and peppermint essential oil.

9. The eye care composition containing L-ergothioneine according to claim 8, wherein the plant essential oil is selected from at least one of the chamomile essential oil and the peppermint essential oil.

10. The eye care composition containing L-ergothioneine according to claim 1, wherein the osmotic pressure regulator is selected from at least one of sodium chloride, potassium chloride, sorbitol, borax and boric acid.

* * * * *